United States Patent [19]

Mehdian

[11] Patent Number: 4,998,936

[45] Date of Patent: Mar. 12, 1991

[54] APPARATUS FOR USE IN THE TREATMENT OF SPINAL DISORDERS

[76] Inventor: Seyed M. H. Mehdian, Robert Jones & Agnes Hunt Orthopaedic Hospital, Department of Spinal Disorders, Oswestry, Shropshire, SY10 7AG, England

[21] Appl. No.: 225,767

[22] Filed: Jul. 29, 1988

[30] Foreign Application Priority Data

Aug. 7, 1987 [GB] United Kingdom ............. 8718708

[51] Int. Cl.⁵ ............................................. A61F 5/01
[52] U.S. Cl. ..................................... 606/61; 606/60; 128/68
[58] Field of Search .................... 606/61, 60, 105; 128/68, 78

[56] References Cited

U.S. PATENT DOCUMENTS

| | | | |
|---|---|---|---|
| 4,289,123 | 9/1981 | Dunn | 606/61 |
| 4,369,769 | 1/1983 | Edwards | 606/61 |
| 4,573,454 | 3/1986 | Hoffman | 606/61 |
| 4,686,970 | 8/1987 | Dove et al. | 606/61 |
| 4,773,402 | 9/1988 | Asher et al. | 606/61 X |

Primary Examiner—Richard J. Apley
Assistant Examiner—Jennifer L. Doyle
Attorney, Agent, or Firm—William E. Mouzavires

[57] ABSTRACT

A crosspiece for use in forming a link or frame to embrace a group of segments of a spinal column in the treatment of spinal disorders has a pair of tubular side members joined by a spacing member intermediate their ends and the axes of the tubular side members and the axis of the spacing member are coplanar. A pair of crosspieces can be combined with a pair of rods to form a link or frame which will cater for spinal growth. The rod members can be plain rods or L-shaped rods or ratchet rods or combinations thereof. The bores in the tubular through bores are closed ended.

26 Claims, 3 Drawing Sheets

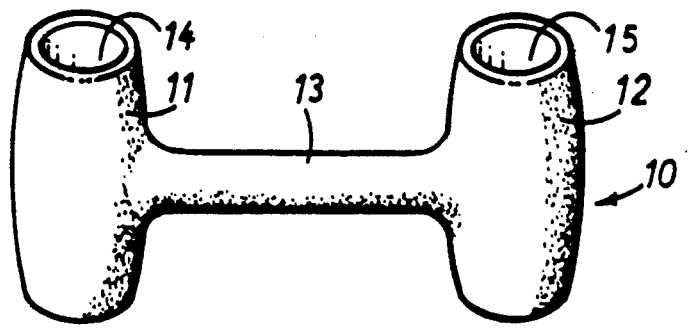
Fig_1
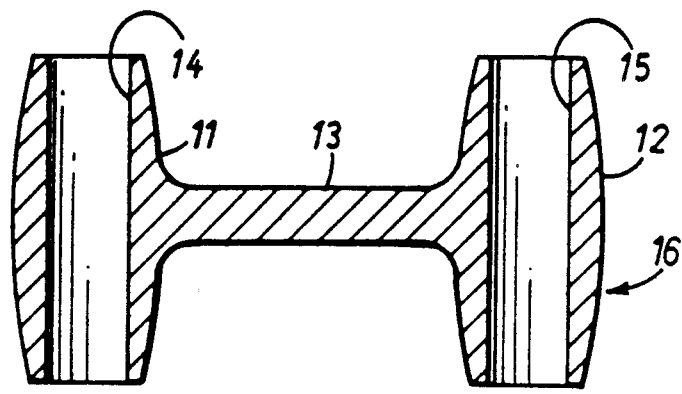
Fig_2
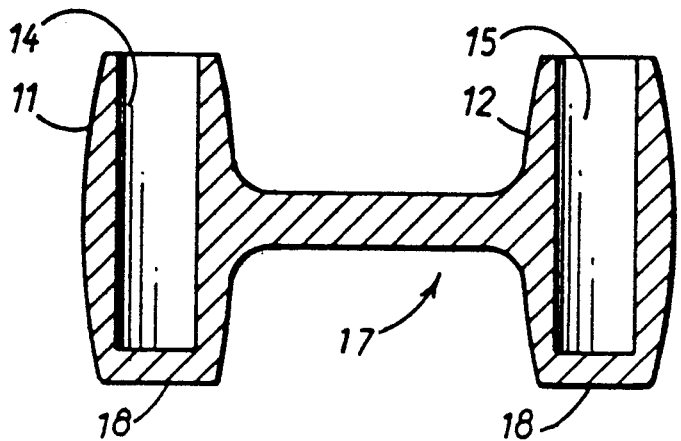
Fig_3
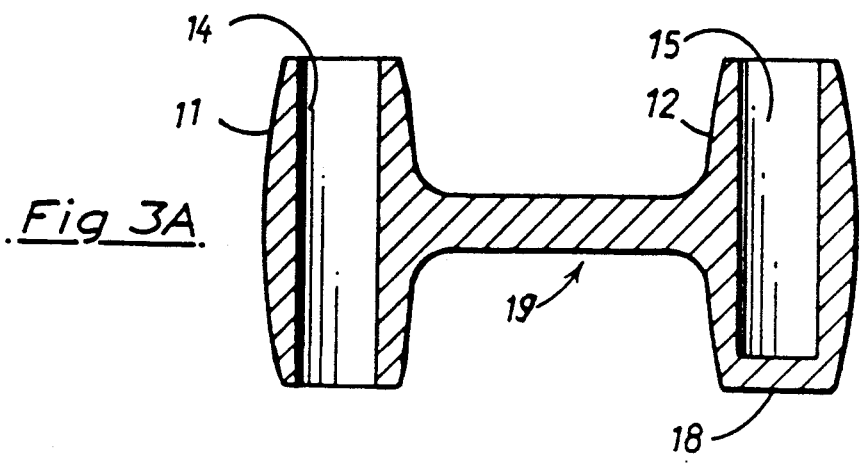
Fig_3A

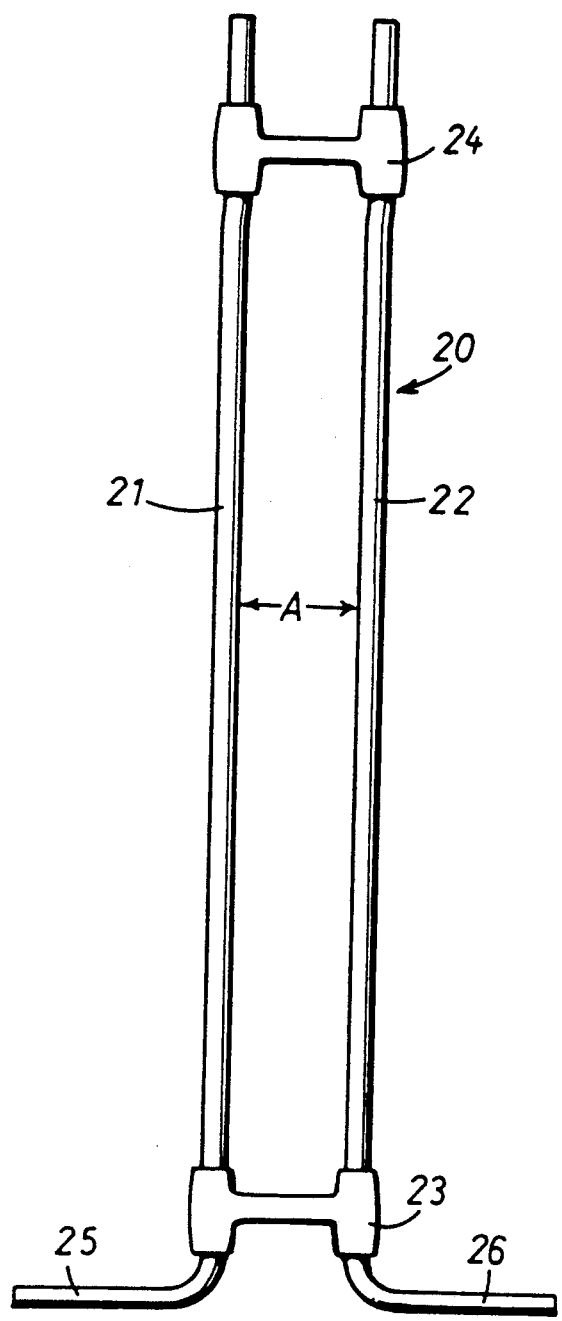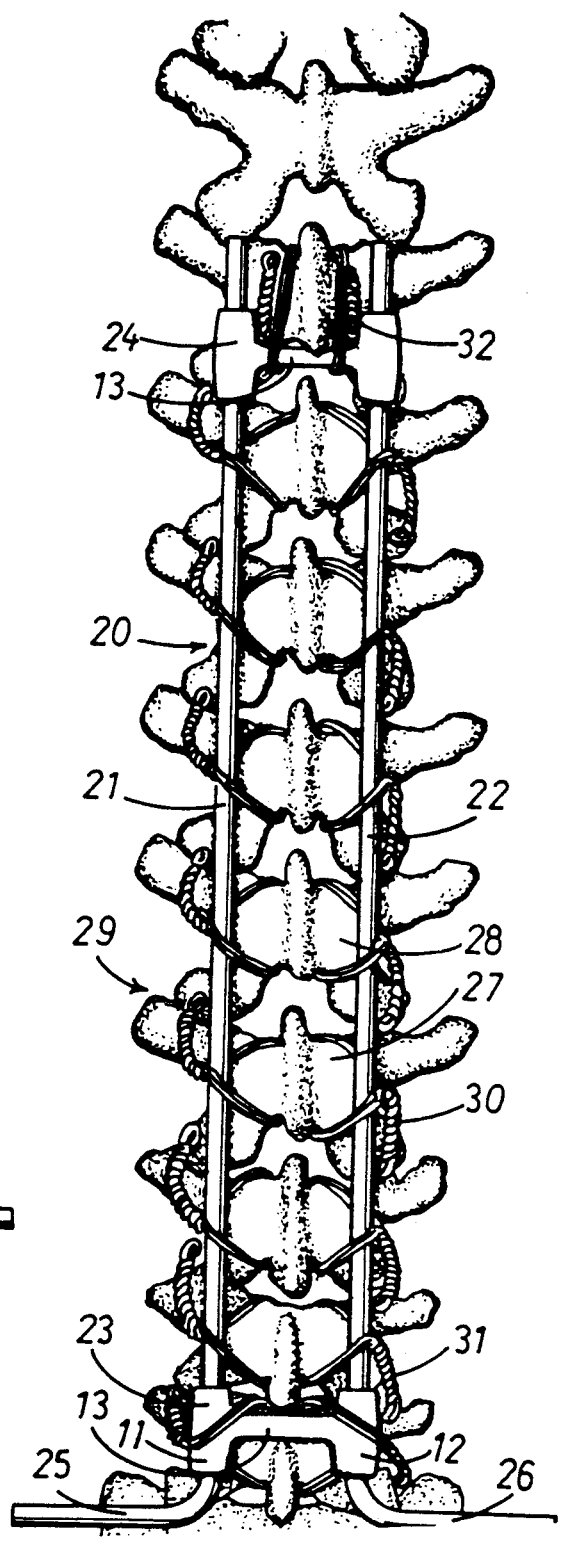
Fig_4.
Fig_5.

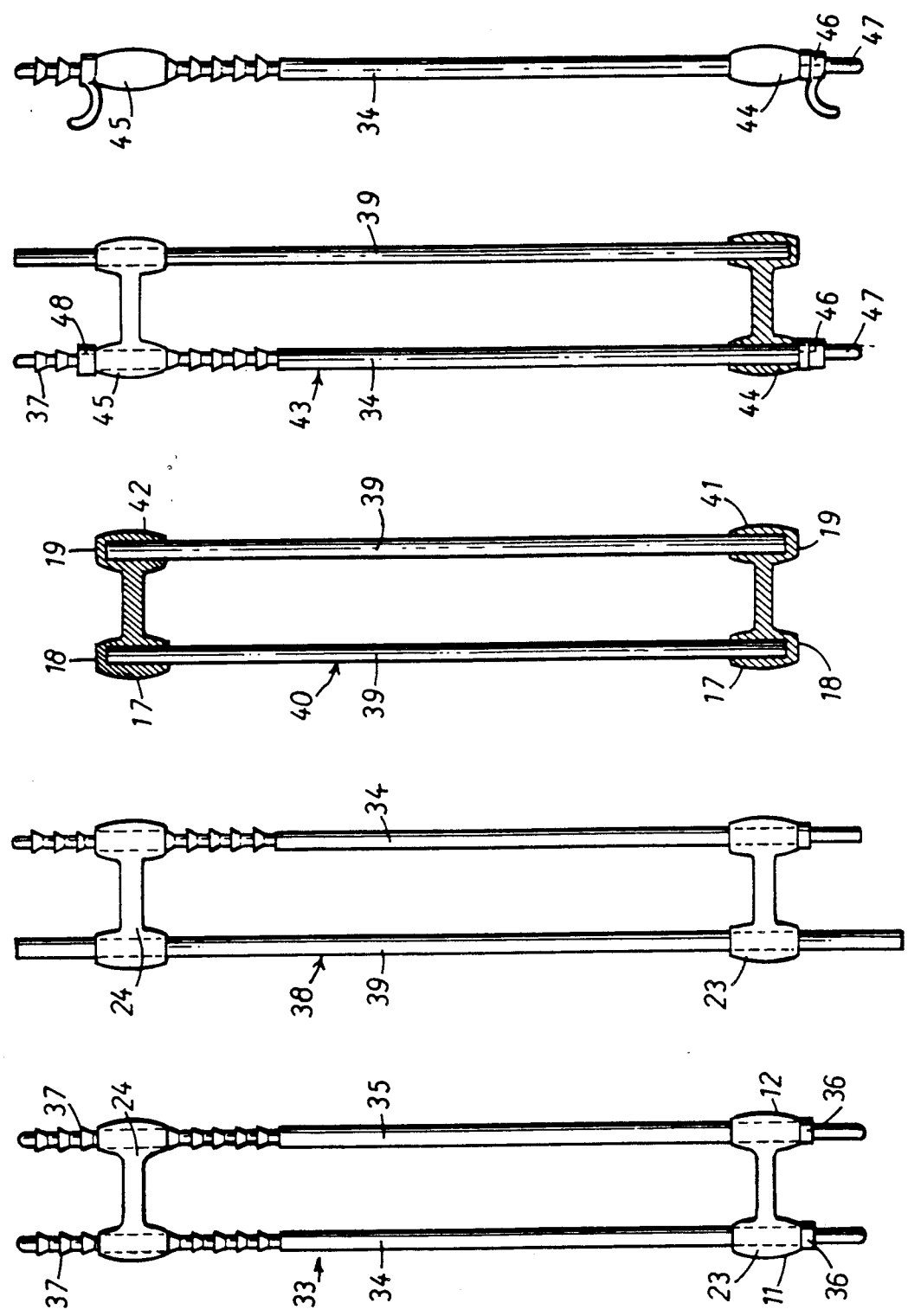

APPARATUS FOR USE IN THE TREATMENT OF SPINAL DISORDERS

DESCRIPTION

The present invention relates to apparatus for use in the treatment of spinal disorders.

In certain methods of treatment of spinal disorders it is desirable to restrict the movement of some segments of the spinal column or to correct the positions of certain segments of the spinal column. In many cases this is done by placing a link or frame around the rear parts of relevant segments of the spinal column and attaching each of the segments concerned to the opposite sides of the link or frame by means of wire ties which are inserted through the centre regions of the segments of the spinal column, that is to say, they are passed under the posterior arches of vertebrae, the ends of each wire tie being twisted together around the link or frame whereby to secure each of the relevant members of the spinal column to the link or frame. The link or frame may comprise a pair of L-shaped rods, one on each side of the spinal column, such rods having the advantage by virtue of their length of not being restricted to a predetermined number of segments of the spinal column but having the disadvantage of permitting some twisting of the spinal column, thereby providing poor control of rotation in spinal stabilisation. Alternatively, the link or frame may be a ring generally rectangular in shape and the long dimension of the ring may be relatively small so that the ring only encompasses a small number of segments, say three or four, or may be of some considerable length so as to encompass a larger number of segments, whilst such a fixed rectangular frame can restrict twisting of the spinal column and thereby provide good control of rotation in spinal stabilisation, it has the disadvantage of not being easily fixed to the pelvis and thereby providing poor fixation in paralytic deformities, and/or also of producing a tethering effect which is particularly undesirable when spinal fixation is required in a growing child since, as the child grows, it is found in practice that breakage or sliding of the very top and very bottom wire ties is inevitable and leads to loss of correction.

There is therefore a need for a link or frame which can cater for spinal growth and one form of telescopic structure has been proposed in U.K. Patent Application No. 2,151,928A. One such structure comprises a first U-shaped member of rod material and a second co-operating U-shaped member with tubular limbs into which the limbs of the first member are telescopically received, whilst a modified structure comprises first and second U-shaped members of rod material and a third member with tubular side limbs into which the limbs of the first and second members are received. The bases of the first and second U-shaped members, and an intermediate member of the third member, are all cranked or bent to enable "roofed" rectangular structures to be formed. Such structures possess a number of disadvantages which dissuade their use: firstly the limbs cannot be bent to the shape of normal physiological curvature of a spinal column: secondly the tubular limbs result in a relatively weak structure as compared with a structure with continuous solid limbs; and thirdly, with increasing length of the structure, the structure becomes weaker because more of the tubular limbs become empty as the rod limbs are withdrawn therefrom.

According to the present invention a crosspiece for use in forming a link or frame adapted to embrace a group of segments of a spinal column in the treatment of spinal disorders comprises a pair of tubular side members with their longitudinal axes substantially parallel with one another and spaced apart, and joined by a spacing member which is disposed intermediate the ends of the tubular side members and which extends substantially at right angles to the longitudinal axes of the tubular side members and has its longitudinal axis substantially coplanar with the longitudinal axes of the tubular side members to form an H-shaped unitary structure, and each of the tubular side members has an axial bore which is open at least one end to receive a rod member, the bores of the two tubular side members being open at the same ends of the tubular side members.

In use a link or frame is formed by a pair of rod members and a pair of crosspieces, with parts of the rod members received in the bores of the side members of the crosspieces.

Preferably both the side members and the spacing member are substantially circular in cross-section and have smooth exterior surfaces. The spacing member can have an external diameter approximating to the internal diameter of the bores in the side members and the ends of the spacing member merge smoothly into the side members.

The axial bores in the tubular side members can be through-bores whereby a crosspiece can be slid onto a pair of rod members, two crosspieces being used to complete a link or frame. Alternatively one or both of the axial bores can be closed-ended so that only the end portion of a rod member is received in that closed-ended bore. Both bores can be closed-ended so that the crosspiece can locate the ends of two rod members. Yet again one axial bore can be closed-ended to receive and locate the end of a rod member whilst the other bore is open-ended so that a second rod member can be slid through it.

The two rod members used to form a link or frame can be plain rods, L-shaped rods (conventionally known as Luque rods), ratchet rods (conventionally known as Harrington rods), or a combination of a plain rod and an L-shaped rod, or of a plain rod and a ratchet rod, depending on the form of correction or stabilisation required and on the age of the patient.

In general it is found that two diameters of rods, namely one quarter inch (6.35 mm) diameter and three sixteenths inch (4.76 mm) diameter, meet most requirements for spinal fixation. Similarly whilst the internal spacing between the rods in a link or frame varies according to the age of a patient, it is believed that most needs can be met with spacings of 15 mm, 20 mm, 25 mm and 30 mm. Accordingly it is envisaged that most needs can be met with a range of eight crosspieces. Tie members as disclosed in my co-pending Patent Application No. 07/219,389, filed Jul. 15, 1989 are particularly suitable for use in securing a link or frame embodying crosspieces of the present invention to segments of a spinal column.

The invention will be further described by way of example with reference to the accompanying drawings, in which:

FIG. 1 is a perspective view of a crosspiece embodying the present invention,

FIG. 2 is a longitudinal cross-sectional view of a crosspiece according to one embodiment of the present invention, FIGS. 3 and 3A are respectively a longitudinal cross-sectional view of a crosspiece according to a second and according to a third embodiment of the invention, FIG. 4 is an elevation of a link or frame formed by two L-shaped rods and two crosspieces of FIG. 2, FIG. 5 is a diagrammatic illustration of the link or frame of FIG. 4 applied to part of a spinal column, FIG. 6 is an elevation of another form of link or frame formed by two ratchet rods and two crosspieces of FIG. 2, FIG. 7 is an elevation of a link or frame formed by one plain rod, one ratchet rod, and two crosspieces of FIG. 2, FIG. 8 is an elevational view, partly in section, of a link or frame formed by two plain rods and two crosspieces of FIG. 3, FIG. 9 is an elevation of yet another link or frame formed by one plain rod, one ratchet rod, opposed hook members, a crosspiece of FIG. 2 and a crosspiece of FIG. 3A and FIG. 10 is a side view of the link or frame of FIG. 9.

Referring first to FIG. 1 of the accompanying drawings a crosspiece 10 embodying the present invention comprises two side members 11,12 spaced apart and joined by a spacing member 13 to form an H-shaped unitary structure. The longitudinal axes of the side members 11,12 are substantially parallel with one another and the axis of the spacing member extends substantially at right angles to the axes of the side members and is substantially coplanar with the axes of the side members. Each of the side members 11,12 has a bore 14,15 which is open at least one end of its respective side member with the open ends being at the same ends of the side members.

In a crosspiece 16 according to a first embodiment of the invention, as illustrated in FIG. 2, both the side members 11,12 have through-bores 14,15 which are open at both ends of the side members. In a crosspiece 17 according to a second embodiment of the invention, as illustrated in FIG. 3, the side members 11,12 have bores 14,15 which are open only at one end of the respective side member, whilst at the other ends of the side members the bores are closed as at 18. In a crosspiece 19 according to a third embodiment of the invention, as illustrated in FIG. 3A, one side member has a through-bore 14 as in the crosspiece 16 of FIG. 2, and the other side member has a closed bore 15,18 as in the crosspiece 17 of FIG. 3.

A crosspiece embodying the present invention can be used with a pair of rods to form a link or frame to embrace and be secured to a number of segments of a spinal column and it is believed that the versatility and advantages of such a crosspiece will be more readily apparent from the following description of links or frames formed with them and the manner in which such links or frames can be used. Such links or frames are particularly suitable for use with wire ties as described in the description of my co-pending Patent Application No. 87 16925.

One form of link or frame 20 is illustrated in FIG. 4 and comprises two L-shaped rods 21,22 (usually known as Luque rods) onto which are slid two crosspieces 23,24. Such link or frame 20 is particularly suitable for use when control of rotation in spinal stabilisation is desired since the sidewardly extending arms 25,26 of the L-shaped rods can be anchored to the pelvis. The lengths of the rods 21,22 and of their arms 25,26 will be selected appropriately in accordance with dimensions of the spinal column to which they are to be affixed and in general it is believed that rods with a diameter of one quarter inch (6.35 mm) or three sixteenths inch (4.76 mm) are sufficient to meet normal stabilisation requirements. Consequently the internal diameters of the bores 14,15 in the side members will correspond to the outside diameters of the rods so that the crosspieces will be a good sliding fit thereon. The side members 11,12 will be spaced apart appropriately to give an internal spacing A between the rods 21,22. In practice suitable spacings are 15 mm, 20 mm, 25 mm or 30 mm. The axial lengths of the side members 11,12 must be long enough to impart sufficient rigidity to the link or frame and at the same time be compatible with the spacing of the segments of the spinal column, and a length of about 20 mm is suitable. The spacing member 13 is preferably of circular cross-section and may conveniently have a diameter approximately equal to the diameter of the bores 14,15. The external surface of a crosspiece is preferably smooth and the junctions between the spacing member 13 and the side members 11,12 are well-rounded so that the spacing member merges into the side members without any abrupt change of direction or surface.

The link or frame 20 of FIG. 4 can be used for stabilisation of a spinal column and one way in which it can be so used is illustrated diagrammatically in FIG. 5. The side arms 25,26 are located on the pelvis and the rods 21,22 extend up on either side of the rear of segments such as 27,28 of the spinal column 29. A series of tie members such as 30 are inserted through the segments of the spinal column and their ends are twisted together to secure each segment concerned to one or other of the rods. In particular wire ties 31,32 are passed around the spacing member 13 or part of the side member 11 or 12 or of the rod 21,22 so as additionally to anchor the crosspiece 23,24 to the pelvis or lowermost segment of the spinal column on the one hand, and to an upper segment of the spinal column on the other hand.

Another form of link or frame 33 which is particularly useful when it is desired to straighten the spinal column by jacking is illustrated in FIG. 6 and comprises a pair of ratchet rods 34,35 (often known as Harrington rods) and a pair of crosspieces 23,24. Each of the rods 34,35 has at one end an enlargement 36 which abuts against the end of a side member 11,12, and at its other end a ratchet section 37. The spacing between the crosspieces 23,24 can be increased in steps by means of the ratchet portions 37 and suitable clamps (not shown) and a known form of hook means can be used to apply tension between the segments of the spinal column. It is not always necessary to employ two ratchet rods and on occasions one may suffice. The frame or link 38 illustrated in FIG. 7 is formed by a plain rod 39, a ratchet rod 34 and a pair of crosspieces 23,24.

When a simple rigid frame which cannot contract lengthwise but can be capable of limited expansion lengthwise is required, crosspieces 17 of FIG. 3 can be used and such a link or frame 40 is illustrated in FIG. 8 and comprises two plain rods 39 and a pair of crosspieces 41,42 each of which has bores which are closed-ended as at 18,19. It will be readily apparent that a crosspiece 16 of FIG. 2 can on occasions be used in place of a crosspiece 17 of FIG. 3 at one end when lengthwise expansion or contraction of the link or frame is permissible.

A still further form of link or frame 43 is illustrated in FIGS. 9 and 10 and comprises a plain rod 39, a ratchet rod 34, a crosspiece 44 at one end, and a crosspiece 45 at the other end. The crosspiece 44 is a crosspiece 19 of FIG. 3A which has one side member with a through-bore and a second side member with a bore closed at one end, whilst the crosspiece 45 is a crosspiece 16 of FIG. 2. For the purpose of applying tension between segments of the spinal column a hook member 46 is slipped onto the lower end 47 of the ratchet member 34 and a similar member 48 is slipped up on to the ratchet end 37 of the ratchet rod 34.

Crosspieces embodying the present invention are versatile and can be used with a variety of arrangements of rods to form a frame or link which is generally rectangular in shape and can be used to provide good rotational control in spinal segmental fixation. Since one or both of the crosspieces forming a link or frame can slide on the rods the longitudinal dimension of the link or frame can increase and thereby avoid the tethering effect of a fixed rectangular link or frame. This is of particular value in the treatment of growing children since when the spine grows the the longitudinal rods can slide in the crosspieces whilst the crosspieces remain fixed to the segments and/or pelvis by the wire ties whereby loss of correction with growth of the spine can be avoided. With a link or frame embodying L-shaped rods it is possible to ensure a secure grip to the pelvis particularly in paralytic spinal deformities which has not hitherto been possible with a fixed dimension rectangular link or frame.

It is not essential for a link or frame to be constructed completely before it is placed in position on a spinal column. When L-shaped rods are used, the rods can be slid into two crosspieces and the rods then bent into the configuration required according to the physiological spinal curvature; the top crosspiece can then be removed from the rods and the rods can then be slid through the tie members which have previously been inserted through the respective segments of the spinal column. The side arm of one of the L-shaped rods can now be fixed to the pelvis and thereafter the side arm of the other L-shaped rod located by a rocking movement and fixed to the pelvis also; next the top crosspiece can be slid back onto the two L-shaped rods leaving at least one inch (25.4 mm) of the rods projecting in order to allow for spinal growth, and the complete link or frame then located as desired and fixed to the segments of the spinal column.

It will be appreciated that at a crosspiece embodying the present invention can enable a rigid parallel segmental fixation for treatment of spinal disorders and injuries to be developed which can provide adequate rotational control and also can avoid the tethering effect of a conventional fixed rectangular link or frame when used in growing children.

I claim:

1. A crosspiece for use in forming a link or frame adapted to embrace a group of segments of a spinal column in the treatment of spinal disorders, said crosspiece comprising:
   a pair of spaced apart tubular side members; and
   a spacing member joining said side members to one another,
   said side members having longitudinal axes, said longitudinal axes being substantially parallel to one another,
   said spacing member being disposed intermediate the ends of said side members and extending substantially at right angles to said side members and being substantially coplanar with said side members to form an H-shaped structure,
   each of said side members having an axial bore which is open at least one end to receive a rod member,
   the bores of said side members being open at the same ends of the side members.

2. A crosspiece for use in forming a link or frame adapted to embrace a group of segments of a spinal column in the treatment of spinal disorders, said crosspiece comprising:
   a pair of tubular side members; and
   a spacing member connected to each of said side members intermediate their ends;
   said side members having longitudinal axes, said longitudinal axes being substantially parallel with one another and substantially coplanar with the axis of the spacing member;
   said spacing member extending substantially at right angles to each of said side members to form an H-shaped unitary structure;
   each of said side members having an axial bore to receive a rod member.

3. A crosspiece as set forth in claim 2, in which at least one of the side members has a through bore.

4. A crosspiece as set forth in claim 2, in which at least one of the side members has a through bore and the bores of the two side members are open at the same ends of the side members.

5. A crosspiece as set forth in claim 2, in which at least one of the side members has a closed ended bore.

6. A crosspiece as set forth in claim 2, in which the bore of each of the side members is closed ended and the bores of the two side members are open at the same ends of the side members.

7. A surgical crosspiece for use in forming a link or frame adapted to embrace a group of segments of a spinal column in the treatment of spinal disorders, said crosspiece comprising:
   a pair of substantially parallel tubular side members; and a spacing member substantially coplanar with the side members and extending between the tubular side members to hold the tubular side members in spaced apart relationship and forming with the side members a generally H-shaped unitary structure to receive rod members, and wherein each of said side members has a bore to receive a rod member.

8. A crosspiece as set forth in claim 7, in which each of the tubular members has a through bore.

9. A crosspiece as set forth in claim 7, in which the bore of one of the tubular side members is closed ended.

10. A crosspiece as set forth in claim 7, in which the spacing member has an external diameter approximately equal to the internal diameter of the bore of a tubular side member.

11. A crosspiece as set forth in claim 10, in which the spacing member merges smoothly into the side members.

12. A crosspiece as set forth in claim 7, in which both the two tubular side members and the spacing member are substantially circular in cross section and have smooth exterior surfaces.

13. A crosspiece as set forth in claim 7, in which the bores of both of the tubular side members are closed ended.

14. A crosspiece as set forth in claim 13, in which the bores of the two tubular side members are open at the same ends of the tubular side members.

15. A crosspiece as set forth in claim 7 wherein said spacing member extends substantially at right angles to each of the tubular side members.

16. A crosspiece as set forth in claim 7 wherein the bores of the two tubular side members are open at the same ends of the tubular side members.

17. A crosspiece as set forth in claim 7 wherein the bore of each side member has a diameter ranging from about three-sixteenths of an inch (4.76 mm) to one-quarter of an inch (6.35 mm).

18. A crosspiece as set forth in claim 7 wherein the bores of the tubular side members are laterally spaced from each other a distance ranging from about 15 mm to 30 mm in order to space rod members to be received in the bores at a predetermined distance from each other.

19. A crosspiece as set forth in claim 17 wherein the bores of the tubular side members are laterally spaced from each other a distance ranging from about 15 mm to 30 mm in order to space rod members to be received in the bores at a predetermined distance from each other.

20. In a link or frame adapted to embrace a group of segments of a spinal column in the treatment of spinal disorders, the combination of a pair of rod members and a pair of crosspieces connecting the rod members together, in which each of said crosspieces comprises:
   a pair of substantially parallel tubular side members,
   a spacing member substantially coplanar with the side members and extending substantially at right angles to each of the side members to hold the tubular side members in spaced apart relationship and form an H-shaped unitary structure to receive the rod members.

21. The combination as set forth in claim 20, in which the rod members are plain rods.

22. The combination as set forth in claim 20, in which the rod members are L-shaped rods.

23. The combination as set forth in claim 20, in which the rod members are ratchet rods.

24. The combination as set forth in claim 20, in which one of the rod members is a plain rod.

25. The combination as set forth in claim 20, in which one of the rod members is an L-shaped rod.

26. The combination as set forth in claim 20, in which one of the rod members is a ratchet rod.

* * * * *